United States Patent [19]

Desmond et al.

[11] Patent Number: 4,914,220

[45] Date of Patent: Apr. 3, 1990

[54] PROCESS FOR SYNTHESIS OF E-2-METHYL-α,β-UNSATURATED ALDEHYDES

[75] Inventors: Richard Desmond, Metuchen; Sander G. Mills, Woodbridge; Ralph P. Volante, East Windsor; Ichiro Shinkai, Westfield, all of N.J.

[73] Assignee: Merck & Co., Inc., Rahway, N.J.

[21] Appl. No.: 316,607

[22] Filed: Feb. 27, 1989

Related U.S. Application Data

[63] Continuation of Ser. No. 197,549, May 23, 1988, abandoned.

[51] Int. Cl.$^4$ .............................. C07F 7/08; C07F 7/18
[52] U.S. Cl. .................................. 556/436; 556/413; 556/423
[58] Field of Search .......................................... 556/436

[56] References Cited

U.S. PATENT DOCUMENTS 4,525,586  6/1985  Aristoff ........................... 556/436 X
4,644,068  2/1987  Shibasaki et al. ............... 556/436 X
4,681,951  7/1987  Shibasaki et al. ............... 556/436 X

OTHER PUBLICATIONS

J. Am. Chem. Soc., 1987, 109, pp. 5031–5033.
Tetrahedron Letters, vol. 29, No. 3, pp. 277–280, 1988.
Tetrahedron Letters, vol. 29, No. 3, pp. 281–283, 1988.
Tetrahedron Letters, No. 1, pp. 7–10, 1976.
Tetrahedron Letters, vol. 26, No. 20, pp. 2391–2394, 1985.
Recl. Trav. Chim. Pays-Bas, 10, pp. 369–370.
Tetrahedron Letters, vol. 24, No. 43, pp. 4695–4698, 1983.
J. Am. Chem. Soc., 1983, 105, pp. 646–648.
J. Org. Chem. 1986, vol. 51, pp. 5111–5123.

Primary Examiner—Paul F. Shaver
Attorney, Agent, or Firm—Melvin Winokur; Robert J. North; Joseph F. DiPrima

[57] ABSTRACT

A process is described for the synthesis of E-2-methyl-α,β-unsaturated aldehydes, which are useful as intermediates in the synthesis of the macrolide structure of the immunosuppressant FK-506. These compounds are also useful as ultraviolet radiation absorbers.

16 Claims, No Drawings

PROCESS FOR SYNTHESIS OF E-2-METHYL-α,β-UNSATURATED ALDEHYDES

This is a continuation of application Ser. No. 197,549, filed May 23, 1988, now abandoned.

BACKGROUND OF THE INVENTION

1. Field of the Invention

This invention relates to a process for producing E-2-methyl-α,β-unsaturated aldehydes useful as ultraviolet radiation absorbers and as intermediates in synthesizing the FK-506 immunosuppressant.

2. Brief Disclosures in the Art

The novel 23-membered tricyclo-macrolide FK-506 very recently isolated and characterized by Tanaka, Kuroda, and co-workers, see JACS, 109, pp. 5031, 1987; and EPO Publication No. 0,184,162, has been shown to possess exceptional immunosuppressive activity. The potential usefulness of such an agent in bone marrow and organ transplantations coupled with its unique structural features has prompted many in the field to initiate an effort towards the total synthesis of FK-506.

In conjunction with our efforts on the synthesis of FK-506, we were confronted with the need for the efficient conversion of the aldehyde 1 (see following Scheme I) to the E-2-methyl-α,β-unsaturated aldehyde 2. For synthetic work in the project see: Askin, D.; Volante, R. P.; Reamer, R. A.; Ryan, K. M.; Shinkai, I. *Tetrahedron Lett.* 1988, 29, 277; Mills, S.; Desmond, R.; Reamer, R. A.; Volante, R. P.; Shinkai, I. *Tetrahedron Lett.* 1988, 29, 281.

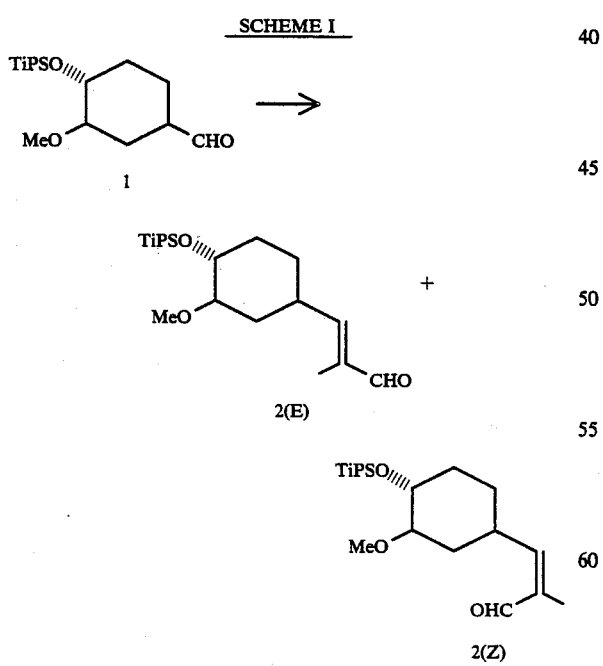

After several unsuccessful attempts, we turned our attention to the procedure of Corey and coworkers as modified by Schlessinger et al., which employed

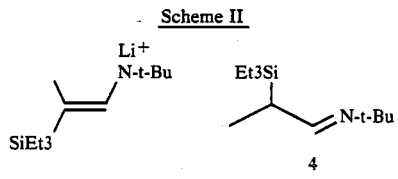

the lithio-silylimine 3, illustrated above in Scheme II. For description of this reagent see: Corey, E. J.; Enders, D.; Bock, M. G. *Tetrahedron Lett.* 1976, 7; Schlessinger, R. H.; Poss, M. A.; Richardson, S.; Lin, P. *Tetrahedron Lett.* 1985, 26, 2391; Meyers, A. I.; Lawson, J. P.; Walker, D. G.; Linderman, R. J. *J. Org. Chem.* 1986, 54, 5111; DeWit, P. P. *Rec. Trav. Chim.* 1984, 103, 369; Takahashi, T.; Kitamura, K.; Tsuji, J. *Tetrahedron Lett.* 1983, 24, 4695; Derguini, F.; Caldwell, C. G.; Motto, M. G.; Balogh-Nair, V.; Nakanishi, K. *J. Am. Chem. Soc.* 1983, 105, 646. However, we found the use of this procedure was not practical as the ratio of E and Z isomers 2(E) and 2(Z) varied unpredictably from 2:1 to 10:1.

What is desired and needed in the art is an overall general synthesis utilizing readily available starting materials which will allow the synthesis of a high yield of the E isomer of 2 in a predictable and desirable E/Z isomer ratio.

SUMMARY OF THE INVENTION

We have found that by utilizing a silylimine analogous to 4 containing a bulky alkyl group on the imine nitrogen, such as cyclohexyl, good yields of the imine II, in high purity can be obtained. Furthermore, we have found that by using a lithium salt of this silylamine II, i.e. IIa, in the condensation step with aldehyde I, a relatively pure mixture of imine condensation products III(Z) and IV(E) can be obtained. We have also surprisingly found that contacting this mixture with anhydrous trifluoroacetic acid, followed by hydrolysis, leads to high yields of the E aldehyde isomer VI.

In accordance with this invention, there is provided a process comprising the steps of:

(a) contacting the aldehyde I:

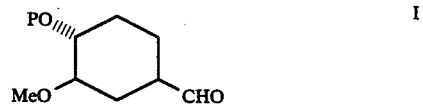

wherein P is a triorganosilyl protecting group, with the imine lithium salt IIa:

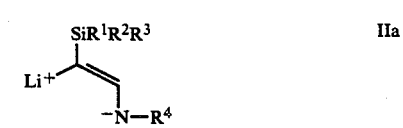

where $R^1$, $R^2$, $R^3$ are independently selected from $C_1$–$C_4$ linear or branched alkyl or phenyl; $R^4$ is $C_3$–$C_8$ secondary or tertiary alkyl, phenyl or substituted phenyl; in an inert organic solvent at $-80°$ C. to $-20°$ C. for a sufficient time to form a mixture of imines III and IV:

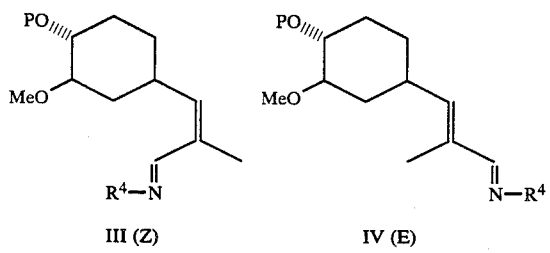

III (Z)      IV (E)

(b) contacting the mixture of imines III and IV from step (a) with anhydrous trifluoroacetic acid at a temperature of −10° C. to +25° C. to substantially convert imine III (Z) to imine IV (E); and (c) contacting the resulting mixture from step (b) with water at a temperature of −5° C. to +25° C. to form the E aldehyde VI:

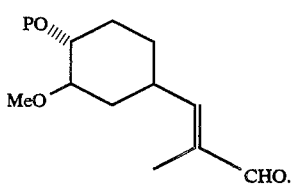

VI

Also provided is a process comprising the steps of:
(a) Contacting a mixture of imines III and IV, where $R^4$ is $C_3$-$C_8$ secondary or tertiary alkyl, phenyl or substituted phenyl, with anhydrous trifluoroacetic acid at a temperature of −10° C. to +25° C. for a sufficient time to substantially convert imine III (Z) to imine IV (E); and

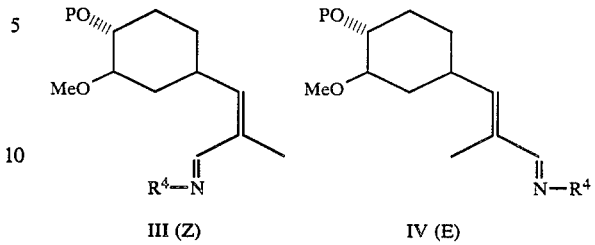

III (Z)      IV (E)

(b) contacting the resulting mixture from step (a) with water at a temperature of −5° C. to +25° C. to form

VI

DETAILED DESCRIPTION OF THE INVENTION AND PREFERRED EMBODIMENTS

The process of the present invention can be readily understood by reference to the following Flow Chart.

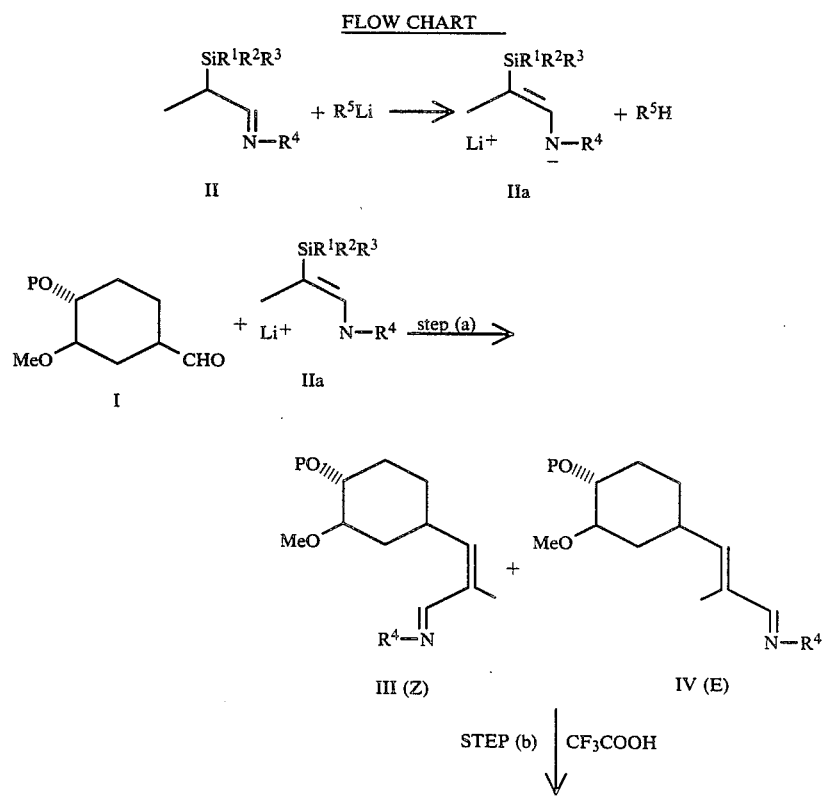

FLOW CHART
-continued

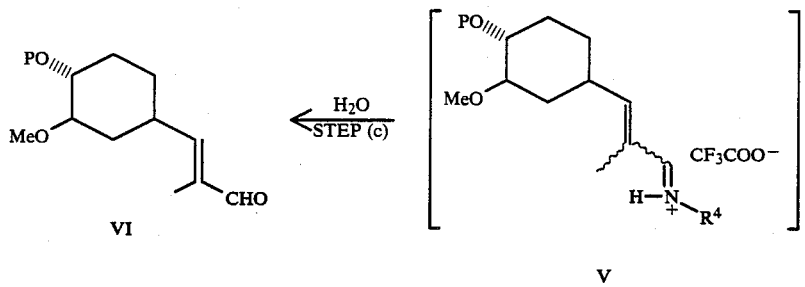

Referring to the above flow scheme, the starting material I is prepared by the procedure of Mills, et al. (see Mills, S.; Desmond, R.; Volante, R. P.; Shinkai, I. *Tetrahedron Lett.*; 1988, 29, 281) hereby incorporated by reference for this purpose.

The symbol, P as used herin, is a conventional silyl hydroxy protecting group known in the art as exemplified in: U.S. Pat. No. 4,616,007; J. F. W. McOmie, "Protective Groups in Organic Chemistry", Plenum Press, London, New York, 1973; T. W. Greene, "Protective Groups in Organic Synthesis", Wiley, New York, 1981; "The Peptides", Vol., Schroeder and Lubke, Academic Press, London, New York, 1965, and Houben-Weyl, "Methoden der Organischen Chemis", Vol. 15/1, Georg Thieme Verlag, Stuttgart, 1974, which are all hereby incorporated by reference for this particular purpose. The references also describe conventional methods for their attachment, use and removal.

All values of P are operable in the illustrated scheme, as a silyl hydroxy protecting group, being a conventional triorganosilyl group in the art, and by the term "organo" is meant $C_2$-$C_6$-alkyl, $C_6$-$C_8$-aryl and $C_3$-$C_{10}$-aralkyl, or mixtures thereof. Representative examples include triethylsilyl, t-butyldimethylsilyl, benzyldimethylsilyl, phenyldiethylsilyl, diphenylmethylsilyl, triisopropylsilyl, triphenylsilyl, and the like. Preferred is triisopropylsilyl.

The scope of applicable materials which can be utilized in the process as I include:

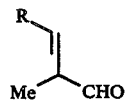

Ia where R=
(a) $C_1$-$C_{10}$ alkyl substituted alkyl;
(b) $C_6$ cycloalkyl and substituted $C_6$ cycloalkyl, of the structure:

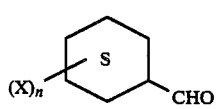

Ib where n is 1–5 and X is independently chosen from F, Cl, Br, H, OH, OMe, OEt, $C_1$-$C_6$ alkyl;
(c) $C_5$ cycloalkyl and substituted $C_5$ cycloalkyl of the structure:

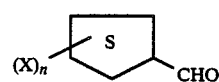

Ic where n is 1–4 and X is as described above;
(d) $C_6$ aromatic and substituted $C_6$ aromatic of the structure:

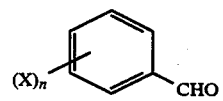

Id where n is 1–5 and X is as described above.

The imine (II) is analogously prepared by the above-cited method of Schlessinger et al., hereby incorporated by reference for this purpose, in which the starting imine has an $R^4$ substituent, i.e. $C_3$-$C_8$ secondary or tertiary alkyl, including cyclohexyl, cyclopentyl, which can be alkyl substituted, thexyl, t-pentyl, t-hexyl; phenyl or substituted phenyl, including 2-alkylphenyl, e.g. o-tolyl, and 2,6-dialkylphenyl, e.g. 2,6-dimethylphenyl, preferred is cyclohexyl. IIa can be prepared, for example, by reaction of the N-$R^4$ alkyl propionaldehyde imine VII, with an organolithium reagent, as shown above, e.g. n-butyllithium, sec-butyllithium, or t-butyllithium, at −78° C. in an inert solvent, e.g. hexane, tetrahydrofuran, ethylether, and an inert atmosphere followed by treatment with a triorganosilylchloride e.g. triethylsilylchloride, trimethylsilylchloride, t-butyldimethylsilylchloride, triisopropylsilylchloride, triphenylsilylchloride. Preferred is triethylsilylchloride. IIa can be prepared in situ, for example, by reaction of II with an organolithium reagent, e.g. n-butyllithium, sec-butyllithium, or t-butyllithium, preferred is sec-butyllithium, at −78° C. in an inert solvent, e.g. hexane, tetrahydrofuran, ethyl ether, and an inert atmosphere.

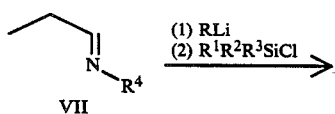

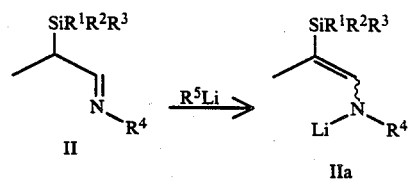

Generally, the reaction of I with IIa in the formation of III and IV mixture is conducted by adding to a solution of the lithium salt of the imine II in an inert, anhydrous organic solvent, e.g. a cyclic or acyclic hydrocarbon including hexane, cyclohexane, and the like, a solution of the aldehyde I in an anhydrous, inert solvent, e.g. tetrahydrofuran, at a temperature of about −78° C. to 0° C. under an inert atmosphere, e.g. dry nitrogen, and stirred for a sufficient time to form the mixture of III and IV.

The lithiating agent is an organolithium, and by the term "organo" is meant where $R^5$ is a $C_1$-$C_6$-alkyl, or aryl lithium, e.g. n-butyllithium, s-butyllithium, methyllithium, isopropyllithium, phenyllithium, and the like, and preferably n-butyllithium and sec-butyllithium.

The imine contains substituents $R^1$, $R^2$, $R^3$ which independently are selected from $C_1$-$C_4$-alkyl, $C_6$-$C_8$-cycloaklyl, $C_6$-$C_8$-aryl, $C_7$-$C_{10}$-aralkyl radicals, or mixtures thereof. The resulting Si $R^1R^2R^3$ radicals include triethylsilyl, triisopropylsilyl, cyclohexyldimethylsilyl, diisopropylcyclohexylsilyl, and the like, and preferably triethylsilyl.

The lithium salt of the imine II mixture is stirred at −80° C. to −30° C. for a period and then a solution of the aldehyde I in an anhydrous inert solvent, e.g. tetrahydrofuran, is added, in an amount such that the molar ratio of the lithium imine salt: aldehyde I is preferably 1.2:1. The solution is allowed to stir at −78° C. to −20° C. for a short while, e.g. 1 hour, or for a sufficient time to form III and IV and then quenched by adding about an equal volume of water. Isolation and purification of the III/IV mixture can be conducted, for example, by extraction into ethyl acetate, followed by water washing, drying over magnesium sulfate, and concentrating in vacuo. Conventional apparatus for conducting the process can be used.

The concentrated mixture of III/IV is then isomerized to maximize the concentration of IV and minimize the presence of III by the use of trifluoroacetic acid. The mixture of III/IV from step (a) is dissolved in a dry, inert solvent such as THF, methylene chloride, hexanes, diethylether and the like, and trifluoroacetic acid is added, preferably dropwise to the solution of III/IV at low temperature in the range of 0° C. to 25° C., in an inert atmosphere, e.g. under nitrogen, argon, and the like. The postulated intermediate V is then treated by the addition of water and the mixture stirred at low temperature, i.e. 0° C. to 25° C., for 10–12 hours. The solution is then treated with aqueous base to neutralize the acid and the formed product VI is extracted by the use of a suitable water immiscible solvent, e.g. ethyl acetate, methylenechloride, chloroform, and the like. Yields of the aldehyde VI are generally in the range of 80 to 95% based on starting I, and the crude aldehyde VI is purified by conventional means.

The following examples are illustrative of the invention and should not be considered as being limitations on the scope of the instant invention.

EXAMPLE 1

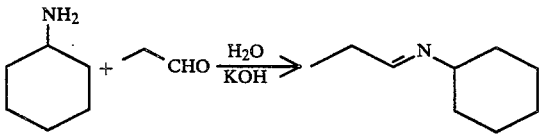

To 361 mL (5.0 mol) of propionaldehyde at 0° C. under a $N_2$ atmosphere was added 572 mL (5.0 mol) of cyclohexylamine over a period of 1.5 hr. The reaction was initially very exothermic, with the temperature rising from 9° to 20° C. upon addition of the first 20 mL of cyclohexylamine, but stabilized at 18° C. after 15 min. for the remainder of the addition.

Upon completion of the addition, the ice bath was removed and the reaction mixture was aged 30–45 min. while warming to room temperature.

The reaction mixture was cooled back to 0° C. and 250 g of crushed KOH pellets was added resulting in a separation of layers. The crude product was then decanted into a flask containing fresh KOH pellets and stored at 0°–5° C. overnight. The crude product was transferred to a distillation flask containing fresh KOH and distilled under house vaccum (2–4 mm Hg) to yield 622 g (89.4%) of propionaldehyde N-cyclohexylimine 5. This procedure can be used to produce propionaldehyde imines for all values of $R^4$. $^1$H NMR (300 MHz, CDCl$_3$, (CH$_3$)$_4$Si): δ 7.62 (t, 1H, J=4.9), 2.90 (t of t, 1H, J=10.5, J=4.2), 2.23 (q of d, 2H, J=7.5, J=4.9), 1.82–1.14 (m, 10H), 1.03 (t, 3H, J=7.5).

EXAMPLE 2

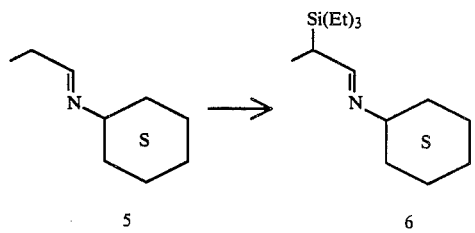

To a −78° C. solution of 215 mL (1.53 mol) of diisopropylamine in 2L of dry tetrahydrofuran under a nitrogen atmosphere was added 935 mL (1.45 mol) of a 1.55M solution of n-butyllithium in hexane over a 30 minute period. The resulting mixture was stirred for an additional 30 minutes upon completion of the addition. To this solution at −78° C. was added 192.2 g (1.38 mol) of the propionaldehyde N-cyclohexylimine 5 over 10 minutes with the internal temperature of the reaction maintained below −60° C. The residual imine was rinsed in with an equal volume of dry tetrahydrofuran, and the resulting mixture was stirred 2 hours at −78° to −70° C. To this solution was added 234 mL (1.39 mol) of chlorotriethylsilane over 10 minutes. The resulting mixture was stirred 15 minutes at −75° C. The external cooling was removed and the reaction was allowed to warm over 1.25 hours to −10° C. Analysis via $^1$H NMR indicated complete reaction. The reaction was quenched by the slow addition of 500 mL H$_2$O and was stirred for 2 hours at 0°–3° C. The reaction mixture was transferred to a separating funnel containing 700 mL of hexanes and the layers were separated. The aqueous layer was extracted with 300 mL hexanes and the combined organic layers were dried over Na$_2$SO$_4$, and concentrated in vacuo to give 350.8 g of crude silylimine 6 as a yellow oil. The crude product was fractionally distilled under vacuum (b.p. 84°–86° C. at 0.1 mmHg) to yield product as a colorless oil in 88% yield. The $^1$H NMR of the distilled material was consistent with the desired product and a small amount of an unidentified impurity (d at 5.95 ppm) did not interfere with the subsequent reaction. $^1$H NMR (300 MHz, CDCl$_3$, (CH$_3$)$_4$Si): δ 7.65 (d, 1H, J=6.7), 2.87 (tt, 1H, J=10.6, 4.1), 2.03 (pentet, 1H, J=7.0), 1.82–1.20 (m, 10H), 1.16 (d, 3H, J=7.0), 0.96 (t, 9H, J=7.8), 0.60 (q, 6H, J=7.9).

This procedure can be used to make all values of SiR¹R²R³ which are operable in the invention.

EXAMPLE 3

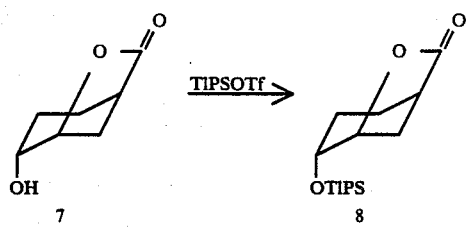

To a solution of 80.1 g (0.563 mol) of the hydroxylactone 7 in 560 mL of dry methylene chloride under nitrogen was added 131 mL (1.125 mol) of 2,6-lutidine. The resulting mixture was cooled to 0° C. and treated dropwise over 30 minutes with 151 mL (0.563 mol) of triisopropylsilyl triflate (TIPSOTF). The reaction was then warmed to room temperature and stirred for 2 hours. The reaction mixture was transferred to a separating funnel containing 2 L of hexanes and washed with 500 mL cold 5% HCl. The organic layer was washed 2 times with 500 mL H₂O, and 500 mL brine. The organic layer was dried over sodium sulfate and concentrated in vacuo to yield 166.4 g (98.9% crude yield) of the TIPS lactone 8 as a yellow oil. The crude product was used without further purification in the subsequent reaction. ¹H NMR (300 MHz, CDCl₃, (CH₃)₄Si): δ 4.60 (t, 1H, J=5.3), 4.20 (m, 1H), 2.58 (m, 1H), 2.45 (d, 1H, J=11.6), 2.22–2.12 (m, 1H), 1.92–1.73 (m, 4H), 1.07 (s, 1H).

EXAMPLE 4

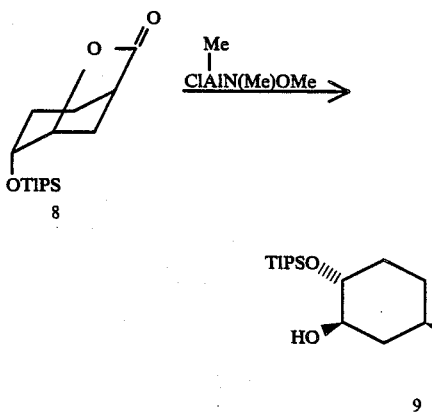

Preparation of Weinreb's Aluminum N-methoxyamide Reagent

To a 0° C. suspension of 117 g (1.13 mol) of N,O-Dimethylhydroxylamine hydrochloride in 650 mL of dry toluene under nitrogen was added dropwise 565 mL (1.13 mol) of a 2M trimethylaluminum/toluene solution. The resulting mixture was warmed to room temperature, stirred 1 hour and the resulting clear, colorless solution was cooled to −20° C. To this solution of the aluminum N-methoxy N-methyl amide was added dropwise a solution of 166.4 g (0.557 mol) of the TIPS-protected lactone 8 in 500 mL of dry tetrahydrofuran. The resulting mixture was warmed to room temperature and stirred for 3 hours. The reaction was transferred via cannula into 1 L of an ice cold, stirred solution of 5% HCl, then the mixture was extracted with 2 L of ethyl acetate. The ethyl acetate was washed with 2 L of H₂O, 500 mL of brine, dried over magnesium sulfate and concentrated in vacuo to 500 mL to give a thick slurry. After an overnight age at 0° C., the product was collected by filtration, the cake was washed with cold hexanes and air dried to yield 147.2 g of a white solid, mp. 89°–92° C. A second crop yielded 15.7 g for a total yield of 162.9 g of 9 (81.3%). The ¹H NMR was consistent with desired product. ¹H NMR (300 MHz, CDCl₃, (CH₃)₄Si), δ 3.70 (s, 3H), 3.67–3.60 (m, 1H), 3.53–3.46 (m, 1H), 3.35 (m, 1H), 3.19 (s, 3H), 2.88 (m, 1H), 2.13–1.95 (m, 2H), 1.89–1.79 (m, 1H), 1.68–1.36 (m, 3H), 1.08 (s, 21H). ¹³C NMR (300 MHz, CDCl₃): δ 176.0, 75.4, 73.5, 61.3, 36.9, 32.4, 30.7, 25.6, 18.0, 17.9, 12.4.

IR(CHCl₃) 2940, 2865, 1640, 1460, 1380, 1200, 1110, 1070 cm⁻¹.

EXAMPLE 5

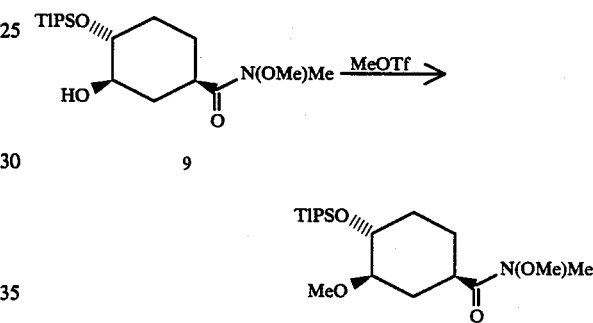

To a solution of 195.1 g (0.95 mol) of 2,6-di-t-butyl-4-methylpyridine in 1 L of dry methylene chloride under nitrogen was added 100 g (0.61 mol) of methyl trifluoromethanesulfonate. The resulting mixture was stirred at room temperature for 2 hours. A solution of 154.7 g (0.43 mol) of the hydroxyamide 9 in 750 mL of dry methylene chloride was then added to the pyridine-methyltriflate solution via cannula at room temperature and the resulting mixture was stirred for 31.5 hours. Analysis via HPLC showed the reaction to be 99.5% complete. The reaction was quenched with 50 mL of MeOH and the resulting mixture was stirred for 5 hours at room temperature. The reaction was concentrated in vacuo with stirring to a volume of 500 mL, and then diluted with 800 mL hexanes. The solid was removed by filtration and the cake was washed with two 500 mL portions of methylene chloride. The filtrate was washed with three 500 mL portions of 10% HCl and with 500 mL H₂O. The combined aqueous washes were extracted with one 500 mL portion of hexanes. The combined organic layer was washed with 500 mL of 3% NaHCO₃, dried over sodium sulfate and concentrated in vacuo to yield 162.5 g (101% crude yield) of product 10 as a pale yellow oil. Analysis via ¹H NMR and LC were consistent with desired product. ¹H NMR (300 MHz, CDCl₃, (CH₃)₄Si): δ 3.70 (s, 3H), 3.60 (m, 1H), 3.37 (s, 3H), 3.17 (s, 3H), 3.00 (m, 1H), 2.71 (app t, 1H), 2.17 (app dg, 1H), 2.01 (m, 1H), 1.73 (m, 1H), 1.67–1.37 (m, 3H), 1.07 (s, 21H). ¹³C NMR (75 MHz, CDCl₃, (CH₃)₄Si): δ 175.5, 84.1, 74.4, 61.3, 57.0, 37.7, 33.7, 32.0, 31.9, 26.8, 17.9, 17.8, 12.8, 12.6, 12.4, 12.0.
IR (film) 2950, 2870, 1670, 1465, 1110 cm⁻¹.

EXAMPLE 6

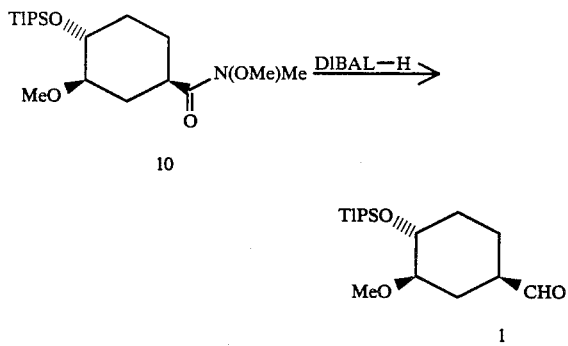

To a −78° C. solution of 100.0 g (0.268 mol) of the amide 10 in 1075 mL of dry tetrahydrofuran under nitrogen was added dropwise 196 mL (0.294 mol) of a 1.5M diisobutylaluminum hydride/toluene solution. The resulting mixture was stirred for 1.5 hours at −78° C. and transferred via cannula into a stirred mixture of 1 L 10% HCl, ice, and 1 L hexanes. The mixture was transferred to a separatory funnel, the layers were separated and the aqueous layer was extracted with two 1 L portions of ethyl acetate. The combined organic layers were dried over sodium sulfate, filtered through a thin pad of celite and concentrated in vacuo to yield 79.8 g (94.8% crude yield) of the aldehyde 1 as a clear yellow oil. ¹H NMR (300 MHz, CDCl₃, Me₄Si): δ 9.67 (s, 1H), 3.76 (m, 1H), 3.35 (s, 3H), 3.16 (m, 1H), 2.3–2.2 (m, 2H), 2.0–1.85 (m, 2H), 1.8–1.55 (m, 2H), 1.44 (m, 1H), 1.07 (s, 21H). ¹³C NMR (75 MHz, CDCl₃, Me₄Si): δ 203.8, 81.2, 70.8, 57.0, 46.1, 29.0, 26.9, 20.7, 18.0, 12.3.
IR (film) 2950, 2870, 1725, 1460, 1110 cm⁻¹.

EXAMPLE 7

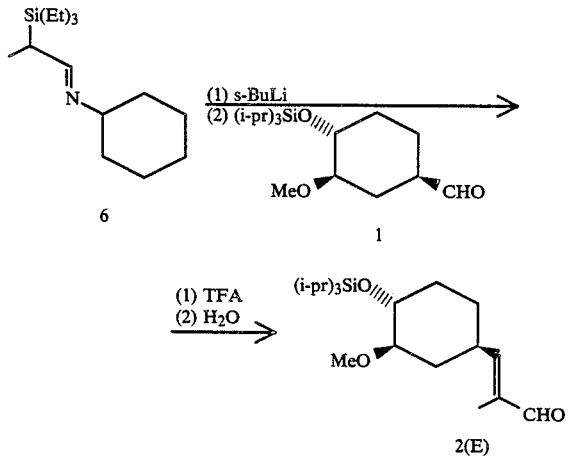

Unsaturated Aldehyde 2: To a −78° solution of 0.366 g (1.44 mmol) of the imine 6 in 2 mL of THF under nitrogen was added 1.02 mL (1.33 mmol) of a 1.3M sec-butyllithium/cyclohexane solution dropwise. The reaction was stirred at −78° C. for 30 min and then was treated with 0.349 g (1.11 mmol) of the aldehyde 1 in 1 mL of THF. The mixture was warmed to −20° C. and was stirred for 1 h. The reaction was quenched with 2 mL of water, and the resulting mixture was extracted with 2×20 mL of ethyl acetate. The combined organic extracts were washed with brine, dried with magnesium sulfate, and concentrated in vacuo. The trifluoroacetic acid isomerization procedure was conducted by dissolving the residue in 5 mL of THF and treating the solution at 0° C. with 0.10 mL (1.323 mmol) of trifluoroacetic acid dropwise under nitrogen. After one hour at 0° C. 2 mL of water were added, and the mixture was stirred at 0° C. for 12 hours. The reaction was poured into a saturated aqueous sodium bicarbonate solution and was extracted with 25 mL of ethyl acetate. The organic phase was washed with brine, dried over magnesium sulfate, and concentrated in vacuo. The residue was purified by flash chromatography with 7% ethyl acetate/hexanes to give 0.329 g (84%) of the unsaturated aldehyde 2(E). Chemical name: E-2-methyl-3-1R, 3R, 4R-(3'-methoxy-4'-triisopropylsilyloxy-1'-cyclohexyl) propenal. ¹H NMR (300 MHz, CDCl₃, (CH₃)₄Si): δ 9.38 (s, 1H), δ 6.31 (d, 1H, J=9.5), δ 3.65 (m, 1H), δ 3.39 (s, 3H), δ 3.06 (m, 1H), δ 2.60 (m, 1H), δ 2.12–1.97 (m, 2H), δ 1.77 (s, 3H), δ 1.76–1.11 (m, 4H), δ 1.08 (s, 21H). ¹³C NMR (300 MHz, CDCl₃): δ 195.5, 157.4, 137.9, 83.6, 74.1, 57.5, 35.8, 34.3, 33.1, 29.2, 18.1, 12.6, 9.3.
IR (film) 2935, 2865, 1690, 1640, 1455, 1380, 1140, 1110, 1080 cm⁻¹.

EXAMPLE 8

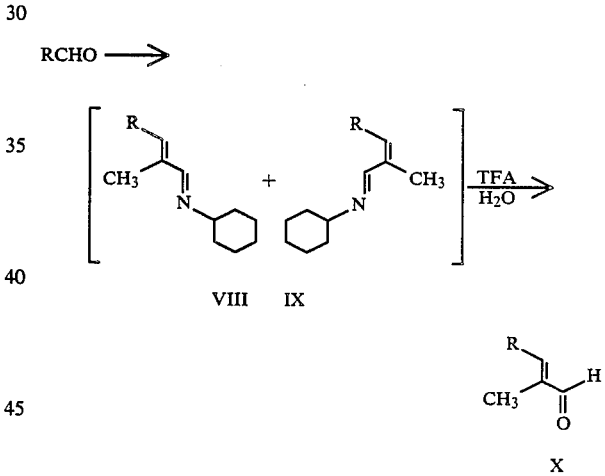

The trifluoroacetic acid isomerization procedure described above was repeated with a variety of substrates, and it was found that when coupled with the use of the secondary butyllithium salt of N-cyclohexyl-imine 6, described in Example 7, reproducibly good yields of E-methyl-α,β-unsaturated aldehydes can be obtained with excellent selectivities (See following Table). Method A, referred to in the Table is the same as described above; Method B is the same except oxalic acid was used in the hydrolysis. Although other methods to isomerize unsaturated carbonyl compounds are known, this protocol has the particular advantage that the species being equilibrated are (presumably) the bulky protonated imines V, which possess a greater steric bias than the parent aldehydes. In addition, we have observed that the Z aldehyde 2(Z) can be transformed into the imines III and IV under standard dehydrating conditions, and application of the usual isomerization conditions then produces a high ratio of E to Z product (IV/III). UV: λmax EtOH=230 nm (Emax=18,500).

TABLE

The reaction of the sec-butyllithium salt of 6 with various aldehydes

| RCHO | Crude E:Z Isomer Ratio[b]:(Yield)[c] | |
|---|---|---|
| | Method[a] A | Method[a] B |
| TPSO/H₃C-cyclohexyl-OHC | 100:1 (84%) | 2:1 (85%) |
| cyclohexene | >100:1 (85%)[d]* | 11:1 (—) |
| CH₃O-C₆H₄-OHC | >100:1 (87%) | 1.3:1 (91%) |
| C₆H₅-OHC | >100:1 (91%)* | 2:1 (—) |
| hexyl-OHC | >100:1 (82%) | 6:1 (83%) |
| TPS/H₃C-cyclohexyl-vinyl-OHC | >100:1 (68%) | 2:1 (—) |

[a]Method A: Anhydrous isomerization with trifluoroacetic acid followed by aqueous hydrolysis; Method B: Hydrolysis with aqueous oxalic acid.
[b]Determined by ¹H NMR at 300 MHz.
[c]Yields for Method A are for the chromatographed E isomer; yields for Method B are for combined E and Z isomers.
Yields with asterisks were determined by quantitative HPLC analysis (25 cm Zorbax SIL column, 35° C., eluant 94:6 hexane:ethyl acetate at 2 mL/min; detection at 230 nm).
[d]Reaction performed with the lithio-t-butylimine 3.

What is claimed is:
1. A process comprising the steps of:
(a) contacting the aldehyde I:

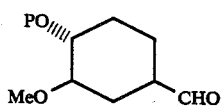

where P is a triorganosilyl protecting group, with the imine lithium salt IIa:

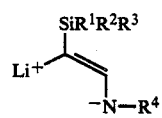

where $R^1$, $R^2$, $R^3$ are independently selected from $C_1$–$C_4$ linear or branched alkyl or phenyl, and $R^4$ is $C_3$–$C_8$ secondary or tertiary alkyl, phenyl or substituted phenyl; in an inert organic solvent at −80° C. to −20° C. for a sufficient time to form a mixture of imines III and IV;

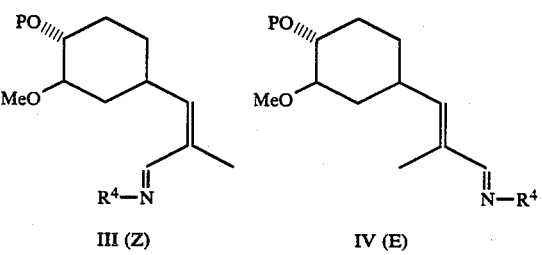

(b) contacting the mixture of imines III and IV from step (a) with anhydrous trifluoroacetic acid at a temperature of −10° C. to +25° C. for a sufficient time to substantially convert imine III (Z) to imine IV (E); and
(c) contacting the resulting mixture from step (b) with water at a temperature of −0° C. to +25° C. to form

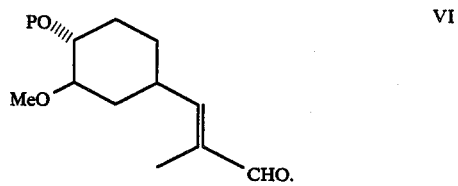

2. The process of claim 1 wherein the temperature in step (a) is −80° C. to −60° C., the temperature in step (b) is −5° C. to +5° C., and the temperature in step (c) is 0° C. to 5° C.
3. The process of claim 1 wherein P is selected from triisopropylsilyl, triethylsilyl, t-butyldimethylsilyl, triphenylsilyl, tribenzylsilyl, or t-butyldiphenylsilyl.
4. The process of claim 3 wherein P is triisopropylsilyl.
5. The process of claim 1 wherein $R^1$, $R^2$, $R^3$ are independently selected from methyl, ethyl, isopropyl, t-butyl, phenyl or benzyl.
6. The process of claim 5 wherein $R^1$, $R^2$, $R^3$ are all ethyl.
7. The process of claim 1 wherein $R^4$ is cyclopentyl, cyclohexyl, thexyl, t-pentyl, t-hexyl, phenyl, o-tolyl and 2,6-dimethylphenyl.
8. The process of claim 7 wherein $R^4$ is cyclohexyl.
9. A process comprising the steps of
(a) contacting a mixture of imines III and IV where $R^4$ is $C_3$–$C_8$ secondary or tertiary alkyl with anhydrous trifluoroacetic acid at a temperature of −10° C. to +25° C. for a sufficient time to substantially convert imine III (Z) to imine IV (E); and

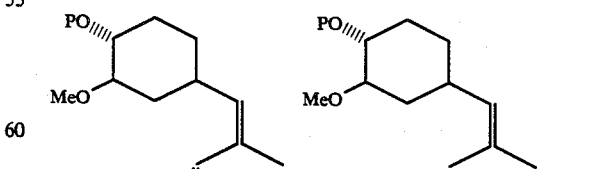

(b) contacting the resulting mixture from step (a) with water at a temperature of −5° C. to +25° C. to form

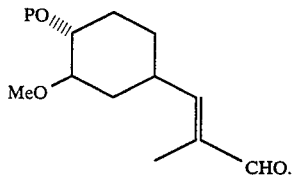

VI

10. The process of claim 9 wherein the temperature in step (a) is −10° C. to +25° C., and the temperature in step (b) is −5° C. to +25° C.

11. The process of claim 9 wherein P is selected from triisopropylsilyl, triethylsilyl, t-butyldimethylsilyl, triphenylsilyl, tribenzylsilyl, or t-butyldiphenylsilyl.

12. The process of claim 11 wherein P is triisopropylsilyl.

13. The process of claim 9 wherein $R^1$, $R^2$, $R^3$ are independently selected from methyl, ethyl, isopropyl, t-butyl, phenyl or benzyl.

14. The process of claim 9 wherein $R^1$, $R^2$, $R^3$ are all ethyl.

15. The process of claim 9 wherein $R^4$ is cyclopentyl, cyclohexyl, thexyl, t-pentyl, t-hexyl, phenyl, o-tolyl or 2,6-dimethylphenyl.

16. The process of claim 7 wherein $R^4$ is cyclohexyl.

* * * * *